(12) United States Patent
Greenwald et al.

(10) Patent No.: US 11,523,867 B2
(45) Date of Patent: Dec. 13, 2022

(54) SYSTEMS AND METHODS FOR IMPLANTATION OF SPINAL PLATE

(71) Applicant: MAKO Surgical Corp., Ft. Lauderdale, FL (US)

(72) Inventors: Jonathan Greenwald, Ft. Lauderdale, FL (US); Ron Irwin, Stuart, FL (US)

(73) Assignee: MAKO Surgical Corp., Ft. Lauderdale, FL (US)

( * ) Notice: Subject to any disclaimer, the term of this patent is extended or adjusted under 35 U.S.C. 154(b) by 66 days.

(21) Appl. No.: 16/736,614

(22) Filed: Jan. 7, 2020

(65) Prior Publication Data
US 2020/0138523 A1    May 7, 2020

Related U.S. Application Data

(60) Continuation of application No. 16/025,462, filed on Jul. 2, 2018, now Pat. No. 10,568,698, and a division
(Continued)

(51) Int. Cl.
| | |
|---|---|
| *A61B 34/00* | (2016.01) |
| *A61B 17/80* | (2006.01) |
| *A61B 34/10* | (2016.01) |
| *A61B 17/16* | (2006.01) |
| *A61B 17/02* | (2006.01) |
| *A61B 17/70* | (2006.01) |
| *A61F 2/44* | (2006.01) |
| *A61B 34/37* | (2016.01) |

(Continued)

(52) U.S. Cl.
CPC ............ *A61B 34/10* (2016.02); *A61B 17/025* (2013.01); *A61B 17/1671* (2013.01); *A61B 17/7059* (2013.01); *A61B 17/808* (2013.01); *A61B 34/20* (2016.02); *A61B 34/30* (2016.02); *A61B 34/37* (2016.02); *A61B 34/76* (2016.02); *A61F 2/442* (2013.01); *A61B 2017/00119* (2013.01); *A61B 2017/564* (2013.01); *A61B 2034/107* (2016.02); *A61B 2034/2055* (2016.02); *A61B 2034/2059* (2016.02); *A61B 2090/065* (2016.02); *A61B 2090/502* (2016.02)

(58) Field of Classification Search
CPC ............ A61B 34/20; A61B 2034/2055; A61B 17/1671; A61B 17/808; A61B 2034/2046; A61B 2034/2059; A61B 2034/2051
See application file for complete search history.

(56) References Cited

U.S. PATENT DOCUMENTS

| | | | |
|---|---|---|---|
| 6,746,450 B1 | 6/2004 | Wall et al. | |
| 8,010,180 B2 * | 8/2011 | Quaid | A61B 34/35 600/426 |

(Continued)

OTHER PUBLICATIONS

International Search Report and Written Opinion for PCT Application No. PCT/US2014/072710, dated Mar. 25, 2015, 14 pages.

*Primary Examiner* — Julianna N Harvey
(74) *Attorney, Agent, or Firm* — Foley & Lardner LLP

(57) ABSTRACT

A method includes tracking one or more of a plurality of vertebrae of a patient, planning a planned alignment of the plurality of vertebrae, creating an implant placement plan based on the planned alignment, and robotically preparing the plurality of vertebrae to receive an implant in accordance with the implant placement plan.

22 Claims, 7 Drawing Sheets

Related U.S. Application Data of application No. 14/586,192, filed on Dec. 30, 2014, now Pat. No. 10,034,711.

(60) Provisional application No. 61/922,627, filed on Dec. 31, 2013.

(51) Int. Cl.
*A61B 34/20* (2016.01)
*A61B 34/30* (2016.01)
*A61B 17/00* (2006.01)
*A61B 17/56* (2006.01)
*A61B 90/50* (2016.01)
*A61B 90/00* (2016.01)

(56) References Cited

U.S. PATENT DOCUMENTS

| | | | |
|---|---|---|---|
| 8,911,501 | B2 | 12/2014 | Irwin et al. |
| D744,103 | S | 11/2015 | Irwin et al. |
| D744,104 | S | 11/2015 | Bechtold et al. |
| D745,158 | S | 12/2015 | Irwin et al. |
| 2003/0233094 | A1* | 12/2003 | Squires ............... A61B 17/025 606/280 |
| 2006/0036264 | A1* | 2/2006 | Selover ............... A61B 90/11 606/130 |
| 2009/0234217 | A1* | 9/2009 | Mire ................... A61B 34/20 600/407 |
| 2010/0191088 | A1* | 7/2010 | Anderson ............ A61B 34/20 606/300 |
| 2010/0217336 | A1* | 8/2010 | Crawford ............ G16H 50/50 606/86 R |
| 2011/0082462 | A1 | 4/2011 | Suarez et al. |
| 2011/0208256 | A1 | 8/2011 | Zuhars |
| 2013/0096573 | A1 | 4/2013 | Kang et al. |
| 2013/0173008 | A1 | 7/2013 | Bechtold et al. |
| 2014/0214086 | A1 | 7/2014 | Benson et al. |

\* cited by examiner

SYSTEMS AND METHODS FOR IMPLANTATION OF SPINAL PLATE

CROSS-REFERENCE TO RELATED APPLICATIONS

This application is a continuation of U.S. patent application Ser. No. 16/025,462, filed Jul. 2, 2018, which is a divisional of U.S. patent application Ser. No. 14/586,192, filed Dec. 30, 2014, which claims the benefit of and priority to U.S. Provisional Patent Application No. 61/922,627, filed Dec. 31, 2013, each of which is hereby incorporated by reference in its entirety.

BACKGROUND

The present invention relates to a surgical system and, more particularly, to a surgical system and method for spinal implant procedures, such as cervical or lumbar discectomy.

Instability of the human spine often calls for the implantation of spinal plates. In the cervical spine, instability may be caused by trauma or deformities, such as curves of the spine, or instability associated with corpectomy for disc disease or with reconstructive surgeries for, as an example, tumors of the cervical spine. A spinal plate, typically used in conjunction with a disc or vertebral prosthesis or a spinal cage/spacer, is used to provide stability between adjacent vertebrae, as well as to maintain a desired rigid relationship between the adjacent vertebrae. Present spinal plates may have a protruding profile when implanted on the spine. For example, a cervical plate often protrudes and causes discomfort for patients. Patients may experience difficulty swallowing, and may feel pressure at their throat. Similarly, protruding plates in the lumbar spine may affect the vascular anatomy in the lower lumbar area. Thus, as an alternative in order to lessen the protrusion of spinal plates, some plates have been designed to be less robust. Plates have been made to be thinner, and therefore less strong, in favor of a lower profile.

Generally, implantation of spinal plates has not been widely performed using computer-assisted surgery systems. The functions of a computer-assisted surgery (CAS) system may include pre-operative planning of a procedure, presenting pre-operative diagnostic information and images in useful formats, presenting status information about a procedure as it takes place, and enhancing performance.

Robotic systems are often used in applications that require a high degree of accuracy and/or precision, such as surgical procedures or other complex tasks. Such systems may include various types of robots, such as autonomous, tele-operated, and interactive. For some types of surgery, such as joint replacement surgery, interactive systems are preferred because such systems enable a surgeon to maintain direct, hands-on control of the surgical procedure while still achieving a high degree of accuracy and/or precision. For example, in knee replacement surgery, a surgeon can use an interactive, haptically guided robotic arm in a passive manner to sculpt bone to receive a joint implant, such as a knee implant. To sculpt bone, the surgeon manually grasps and manipulates the robotic arm to move a cutting tool (such as a burr) that is coupled to the robotic arm to cut a pocket in the bone. As long as the surgeon maintains a tip of the burr within a predefined virtual cutting boundary defined, for example, by a haptic object, the robotic arm moves freely with low friction and low inertia such that the surgeon perceives the robotic arm as weightless and can move the robotic arm as desired. If the surgeon attempts to move the tip of the burr to cut outside the virtual cutting boundary, however, the robotic arm provides haptic (or other force) feedback that prevents or inhibits the surgeon from moving the tip of the burr beyond the virtual cutting boundary. In this manner, the robotic arm enables highly accurate, repeatable bone cuts.

SUMMARY

One embodiment of the invention relates to a method for implanting a spinal plate during a surgical procedure. The method includes the steps of displaying information about a spinal target region of a patient including target vertebrae on which the implantation is to be performed, inserting a spacing device between two adjacent vertebrae to achieve a desired relationship between the vertebrae, planning placement of a spinal plate on the spinal target region to maintain the desired relationship between two adjacent vertebrae. The desired relationship may include one of a desired orientation of a first vertebrae with respect to a second vertebrae and a desired configuration of a vertebral disc space between the first and second vertebrae. The method further includes defining a virtual cutting boundary on a virtual representation of each of the first and the second vertebrae according to the planned placement of the spinal plate on the spinal target region. The method further includes tracking a position of the surgical cutting tool held by a haptic device as the surgical cutting tool is manually moved by a user to form a sculpted cavity independently on each of the first and the second vertebrae for receiving the spinal plate, and providing haptic feedback to the user indicative of interaction between the surgical cutting tool and the virtual cutting boundary. The sculpted cavity formed according to the virtual cutting boundary may have a depth that is greater than or substantially equal to the thickness of spinal plate. The method may also include implanting the spinal plate on the target vertebrae within the sculpted cavity, such that a top surface of the spinal plate is substantially flush with the surface of the target vertebrae. The virtual cutting boundary may correspond to the shape of the spinal plate and the virtual cutting boundary may correspond to the dimensions of the spinal plate. In this method, the surgical cutting tool may be a surgical burr.

The spinal target region for implantation of the spinal plate may be the cervical region of the spine or may be the lumbar region of the spine. The sculpted cavity may span between two adjacent vertebrae, and may further include a portion of the intervertebral disc space between the two adjacent vertebrae. The sculpted cavity may also further include a plurality of predrilled holes for receiving an engagement member to engage the spinal plate with the bone.

The method of implanting a spinal plate may further include displaying an anatomical image of the anatomy of the patient including a representation of the surgical cutting tool as the surgical cutting tool moves during the surgical procedure.

Another embodiment of the invention relates to a surgical system for implanting a spinal plate, comprising a surgical device holding a surgical tool configured to be manipulated by a user to perform an implantation procedure on a patient and a computer system. The computer system is programmed to associate a virtual object with a desired cavity to be sculpted in a first vertebrae and an adjacent second vertebrae of the patient's spine to enable the surgical device to provide a limit on user manipulation of the surgical tool, based on a relationship between a position of the surgical tool and the desired sculpted cavity. The surgical device includes at least one feedback mechanism configured to supply feedback to the user manipulating the surgical device, and the computer system further programmed to control the at least one feedback device to provide the limit on user manipulation, based on a relationship between a position of the surgical tool and the desired sculpted cavity. The virtual object is associated with the desired cavity that is sized and configured to receive the spinal plate therein, according to a planned placement of the spinal plate to achieve a desired relationship between two adjacent vertebrae. The desired relationship may include one of a desired orientation of a first vertebrae with respect to a second vertebrae and a desired configuration of a vertebral disc space between the first and second vertebrae. The desired cavity may be sized and configured such that the spinal plate has a minimal profile above the surface of the patient's spine when implanted.

The system may further include a detection device for determining a pose of an object, and may also include at least one trackable element detectable by the detected device and configured to be attached to an object to be tracked. The system may also include a display device and wherein the computer system is further programmed to display on the display device at least one of a representation of the target portion of the patient's spine, a representation of the spinal plate implanted on the patient's spine, a representation of the virtual object on the representation of the anatomy, and a representation of the surgical tool on the representation of the anatomy as the surgical tool moves during the surgical procedure.

The surgical tool may be a cutting burr. The computer system further may include a database of spinal plate models such that the virtual object can be associated with the desired cavity that corresponds to the shape and size of the particular spinal plate to be used.

Another embodiment of the invention relates to a spinal plate system. The system comprises a spinal plate having a particular shape and size, a surgical device configured to be manipulated by a user, a surgical tool coupled to the surgical device; and a computing system. The computing system is configured to enable a user to plan placement of the spinal plate on a spinal target region to achieve a desired relationship between two adjacent vertebrae on a spine of a patient, define a virtual cutting boundary on each of the first and the second vertebrae according to the planned placement of the spinal plate on the spinal target region, and manipulate the surgical device to prepare a cavity independently on each of the first and the second vertebrae, wherein the shape and size of the cavity corresponds to the shape and size of the spinal plate in the planned placement. The computing system is further configured to provide a limit on user manipulation of the surgical tool, based on a relationship between a position of the surgical tool and the virtual cutting boundary.

Though the present disclosure refers primarily to spinal plates for implantation between adjacent vertebrae, it is contemplated that the present systems and methods can be applied to other applications wherein it is necessary to maintain a desired relationship between two or more bones. Other applications wherein the disclosed systems and methods may be utilized include, but are not limited to, ankle, hand/wrist, and other joint fusion procedures, and craniofacial fusion procedures.

BRIEF DESCRIPTION OF THE FIGURES

The accompanying drawings, which are incorporated and constitute part of this specification, illustrate exemplary embodiments of the invention.

DETAILED DESCRIPTION

Figure 1:
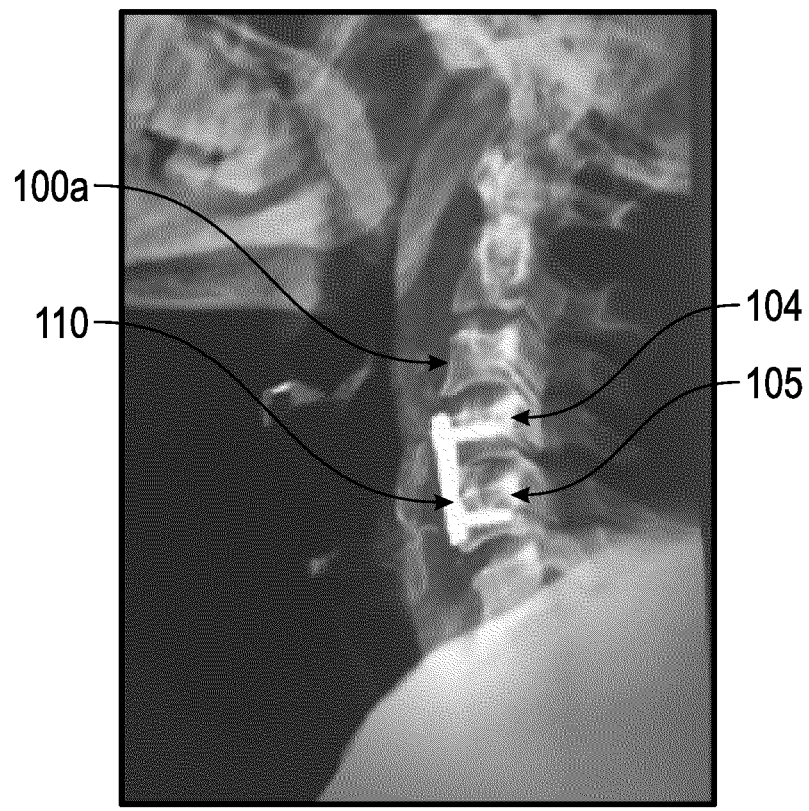
FIG. 1 is a side view of a spinal plate according to the prior art implanted on the cervical spine.

A number of exemplary embodiments of the invention are illustrated in the drawings. An effort has been made to use the same or like reference numbers throughout the drawings to refer to the same or like parts. Although this specification refers primarily to a robotic system for cervical and lumbar spinal plate implantation, it should be understood that the subject matter described herein is applicable to other types of robotic systems and methods, including for other spinal applications.

Referring to FIG. 1, a spinal plate 110, according to currently used devices and methods, is shown implanted on a patient's cervical spine 100. The figure depicts the use of the spinal plate positioned to span from the $4^{th}$ to the $5^{th}$ cervical vertebrae 104, 105, respectively. As shown, the cervical plate 110 protrudes beyond the anterior surface 100a of the cervical vertebrae. For certain patients, this may cause discomfort and potential functional problems (e.g., choking and/or swallowing problems). Similar protrusion may occur with implanted plates on the lumbar spine, which also may cause discomfort and may impact the complex vasculature in the lumbar spine region.

Figure 2:
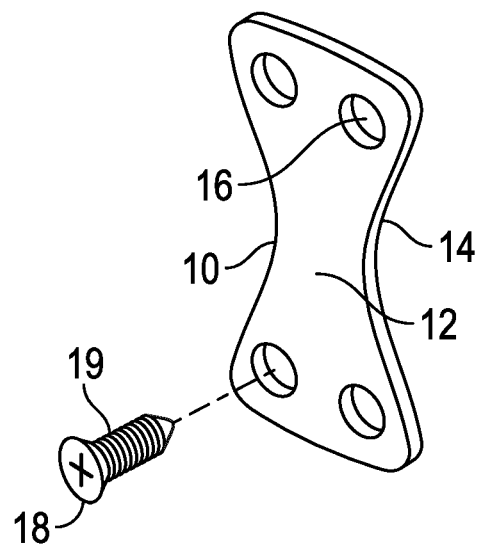
FIG. 2 is a perspective view of a spinal plate according to an exemplary embodiment.

Referring to FIG. 2, a spinal plate 10 according to exemplary embodiments of the present invention is sized and configured to substantially reduce the protrusion of the spinal plate 10 from the vertebrae surface, in connection with the surgical system and methods described below. In the embodiment shown, the spinal plate 10 includes a front surface 12 and a back surface 14. The back surface 14 is configured to be placed in contact with the target vertebrae, such as cervical vertebrae C4 and C5, and span across the intervertebral disc space (shown more particularly in FIG. 5). The spinal plate 10 includes a plurality of engagement apertures 16 for receiving an engagement member 18, such as a screw 19. In the embodiment shown, the spinal plate 10 has two apertures 16 near the top of the plate 10 and two apertures 16 near the bottom of the plate 10 for a total of four apertures, for receiving four engagement members 18. The engagement member 18, such as screw 19, is configured to pass through the engagement aperture 16 from the front surface 12 through the back surface 14, to engage with a hole predrilled in the target vertebrae, and to secure the plate 10 to the vertebrae.

The spinal plate 10 is preferably made of a lightweight, strong material, such as titanium. The spinal plate 10 is of a sufficient thickness to maintain the necessary strength to withstand the forces and pressures on the spinal column without faltering or wearing down. The plate may also be made of a highly porous material, such as the Pourous Structured Technology (PST™) used by MAKO Surgical Corp., to provide high friction for stability and fit, and unique scaffold configuration for cell access. In a preferred embodiment, the spinal plate 10 is thicker than 2.6 mm. This thickness is usually not feasible or desirable due to the profile above the spinal vertebrae surfaces, but can be achieved with spinal plate 10 implanted according to the methods described below.

Figure 3:
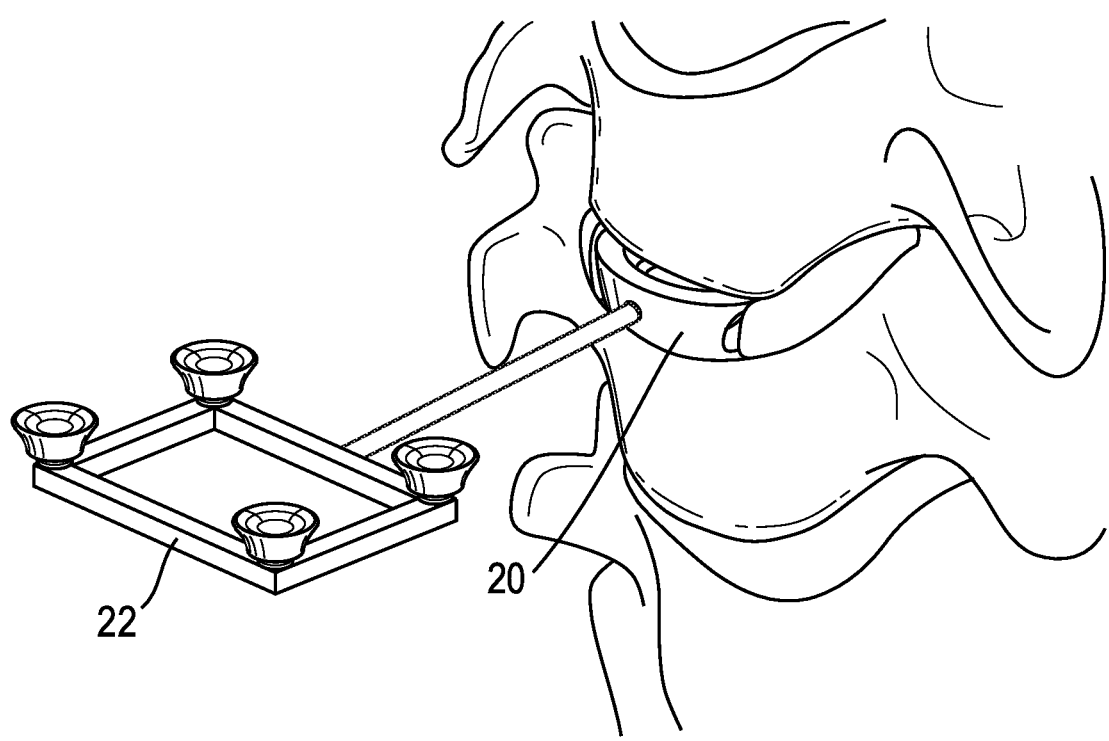
FIG. 3 is a perspective view of a spinal cage inserted between adjacent vertebra and a tracker coupled thereto prior to preparation of the bone to receive a spinal plate.

Prior to implanting the spinal plate 10, a procedure to remove tissue from the disc space is performed. In some cases, it is necessary to clean out diseased annulus tissue. In other cases, a full vertebral body may be removed in a corpectomy procedure. A space is created between vertebrae to receive a spinal cage or spacer, such as cage 20 shown in FIG. 3. Cage 20 is also used in procedures to correct curves of the spine, such as to create a desired distance between portions of adjacent vertebrae to produce improved alignment. With the insertion of a cage 20 between adjacent vertebrae, a desired relationship between the first and second vertrebra can be achieved. The desired relationship may be a desired distance between the two vertebrae (or the height of the intervertebral space), or may be some other relationship of the first vertebrae relative to the second, such as the alignment or the relative rotation between the two (or to prevent changes in the naturally occurring relationship between the adjacent vertebrae, which may be the necessity of the surgical procedure). FIG. 3 depicts cage 20 inserted in vertebral disc space between two adjacent vertebrae to achieved a desired relationship therebetween.

In order to achieve the desired relationship, a first cage 20 may be replaced by a second cage having, for example, a different height, and different cages may be trialed in the space until the proper cage is found to achieve the desired relationship. In some embodiments, the cage 20 may be adjustable, i.e. expandable or adjustable by way of a hinge, to change the height and obtain the desired relationship by adjusting the characteristics of the cage 20. This may be done prior to inserting the cage 20 into the space, or while the cage 20 is positioned between the vertebrae.

In some embodiments, the cage 20 may be further configured to measure forces being applied by each of the adjacent vertebrae. Such information may be useful to understand the conditions of the spine and assist with planning implantation of the spinal plate or other prosthetic components to correct injury, disease or disfigurement of the spine. In one example, an expanding cage can include one or more force sensors to measure the force being applied between the vertebrae as the height of the cage is being manipulated. In this way, the expanding cage can be used as a sort of jack to increase the distance between the vertebrae and measure the force. The force applied between the vertebrae can be measured by a variety of force sensors and measuring apparatuses in association with the cage 20.

Once the cage 20 is inserted and achieves the desired relationship between the adjacent vertebrae, a tracking array 22 may be attached to the cage 20. The tracking array 22 is used to track the position of the cage 20 and the bones (adjacent vertebrae) that are registered thereto, to continuously understand the position and orientation of the vertebrae so that bone preparation to receive the spinal plate 10 can be achieved according to a surgical plan. The tracking system used for this purpose, registration of the bone relative to the tracking array 22, and preparation of the surgical plan to prepare the bone for the spinal plate are discussed in greater detail later in this description.

Figure 4:
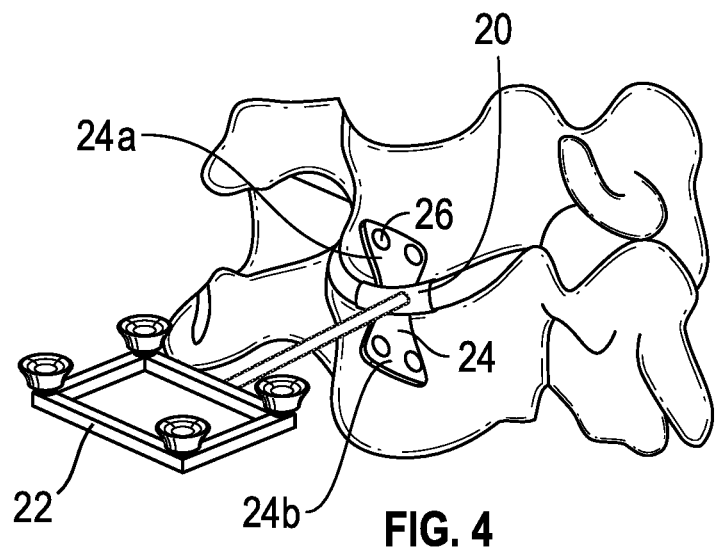
FIG. 4 is a perspective view of a portion of a cervical spine prepared for implantation of a spinal plate.
Figure 5:
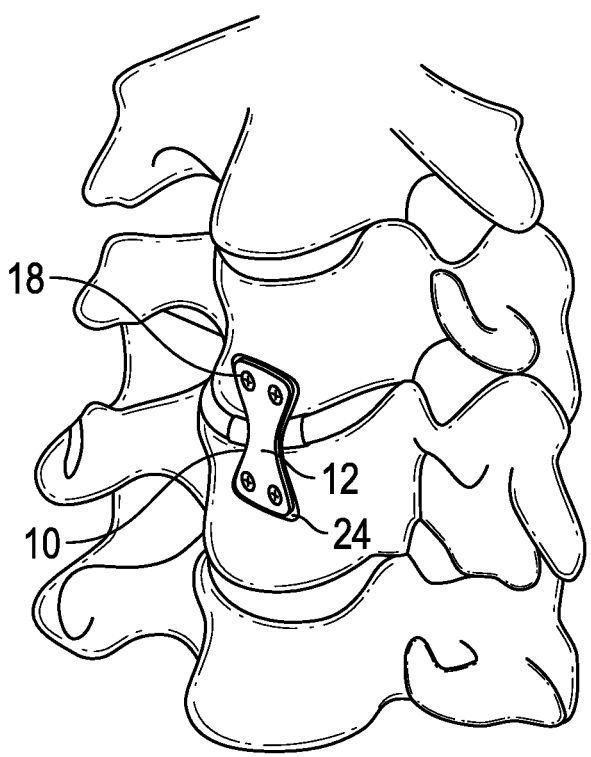
FIG. 5 is a perspective view of a portion of a cervical spine having a spinal plate according to an exemplary embodiment implanted thereon.

As shown in FIGS. 4 and 5, the spinal plate 10 is configured to be received by a sculpted area of bone, which are portions of the bone that have been prepared according to the surgical plan, and based on guidance provided by the tracked position of the bones and the surgical system 30 described below. In particular, the spinal plate 10 can be received within a sculpted cavity 24, formed by cavity portions 24a, 24b, in the two adjacent vertebrae prepared for receiving the plate 10, as shown in FIG. 4. As shown, the cavity 24 corresponds in shape to the plate 10, such as the hourglass shape of the embodiment shown. Further, the cavity 24 is formed to correspond to a planned placement of the spinal plate 10 in order to help maintain the desired relationship between the two adjacent vertebrae. For example, FIG. 5 may represent the desired relationship between the first and the second vertebrae, which the spinal plate is intended to help maintain. Accordingly, each of the cavity portions 24a, 24b is formed in such a way so as to receive the spinal plate 10 that will secure the vertebrae in the desired configuration. Each of cavity portion 24a and 24b is formed independent of the other. In this way, when the spinal plate 10 is implanted in the spine, the implanted spinal plate will hold the adjacent vertebrae in the desired relationship to one another.

There may also be one or more predrilled holes 26 also formed in the bone, corresponding to the number and placement of apertures 16 in the plate 10. Once the sculpted cavity 24 has been formed, the spinal plate 10 can be positioned in the cavity 24 and secured to the bone by at least one engagement member 18. As shown in FIG. 5, in some preferred embodiments, the front surface 12 of the spinal plate 10 is substantially aligned with the surface of the vertebrae, or is positioned within the cavity 24. In this way, there is little to no substantial protrusion of the plate out from the surface of the bone. Thus, the discomfort and risks associated with the plate are minimized, while the plate still is robust enough to maintain the strength and durability needed in spinal applications. In other embodiments, the spinal plate 10 may protrude from the surface of the bone, but nevertheless, the implantation of the plate 10 into the cavity 24 diminishes at least some of the discomfort and other risks associated with spinal plates 10 that are wholly positioned on and protrude from an outer portion of the bone The size, shape, and depth of the cavity 24 sculpted in the bone can be formed to correspond with the various shapes or thicknesses of a variety of differently configured spinal plates 10. Alternatively, a cavity 24 having a general shape with appropriate dimensions to receive the spinal plate 10 may be sculpted into the bone without particular regard to the exact shape of the spinal plate 10.

In certain configurations, the spinal plate and the related systems and methods may be used to secure more than two adjacent vertebrae. In some configurations, the spinal plate may be configured to span more than two vertebrae, to provide for the desired relationship between, for example, three, four, five etc. vertebrae along the spine. During surgical planning (described in further detail below), the appropriate spinal plate is selected and the cavity in the bone is formed in order to accommodate a spinal plate spanning three or more vertebrae. In other configurations, a series of a plurality of spinal plates may be used to secure relative alignment and spacing between a series of vertebrae. In this way, a first spinal plate, such as spinal plate 10, can be positioned to span a first and a second vertebrae, and a second spinal plate spans from the second to the third vertebrae. Surgical planning is then performed to prepare two cavities in, for example, the second vertebrae, to accommodate a portion of both the first and the second spinal plates.

Figure 6:
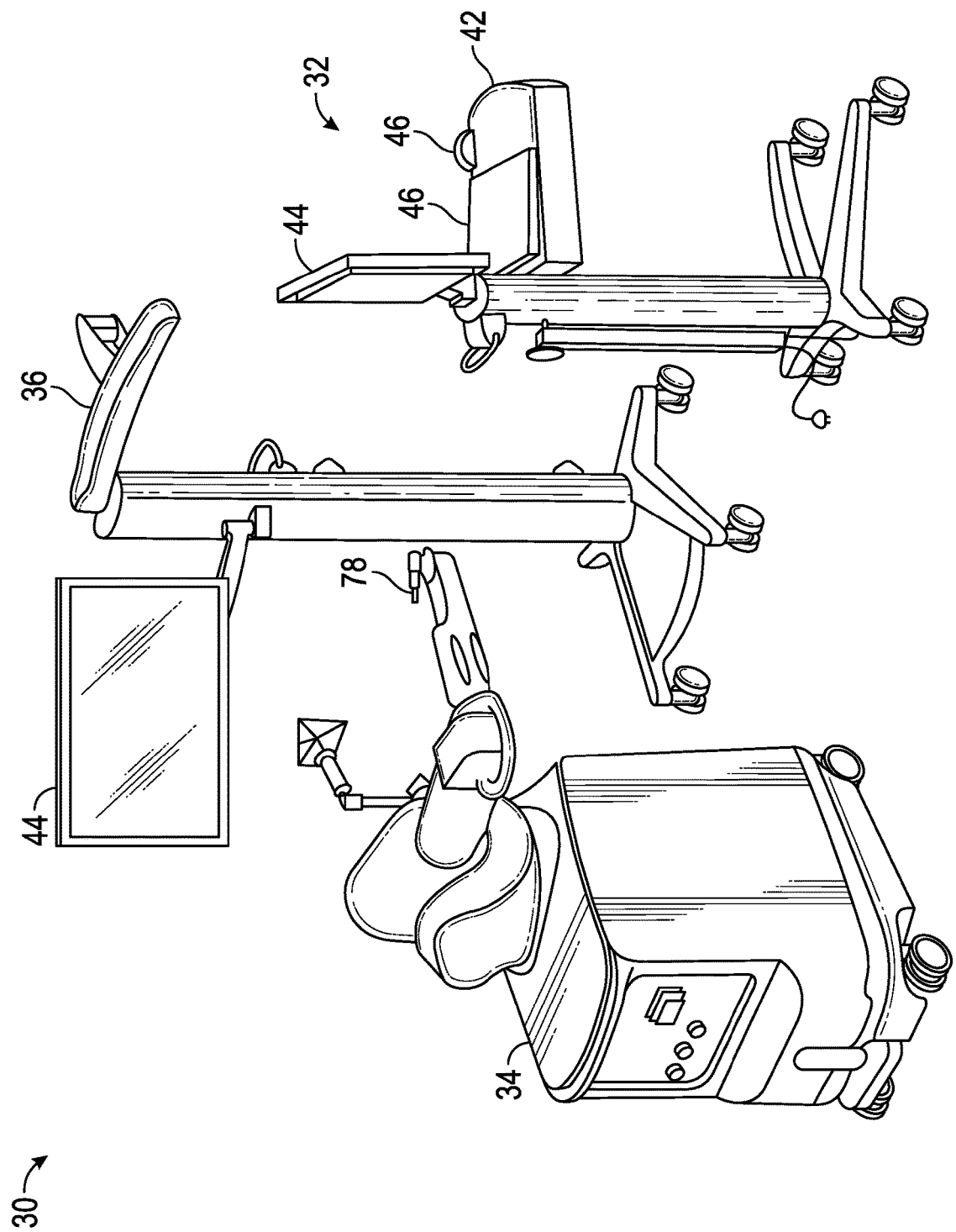
FIG. 6 is a perspective view of an embodiment of a surgical system according to an exemplary embodiment.

FIG. 6 shows an embodiment of an exemplary surgical system 30 in which the techniques described above can be implemented. Such an exemplary system is described in detail, for example, in U.S. Pat. No. 8,010,180, issued Aug. 30, 2011, which is hereby incorporated by reference herein in its entirety. The surgical system 30 includes a computing system 32, a haptic device 34, and a navigation system 36. In operation, the surgical system 30 enables comprehensive, intraoperative surgical planning, such as planning placement of the spinal plate 10 to achieve a desired relationship between two adjacent vertebrae. The surgical system 30 also provides haptic guidance to a user (e.g., a surgeon) and/or limits the user's manipulation of the haptic device 34 as the user performs a surgical procedure.

Figure 7:
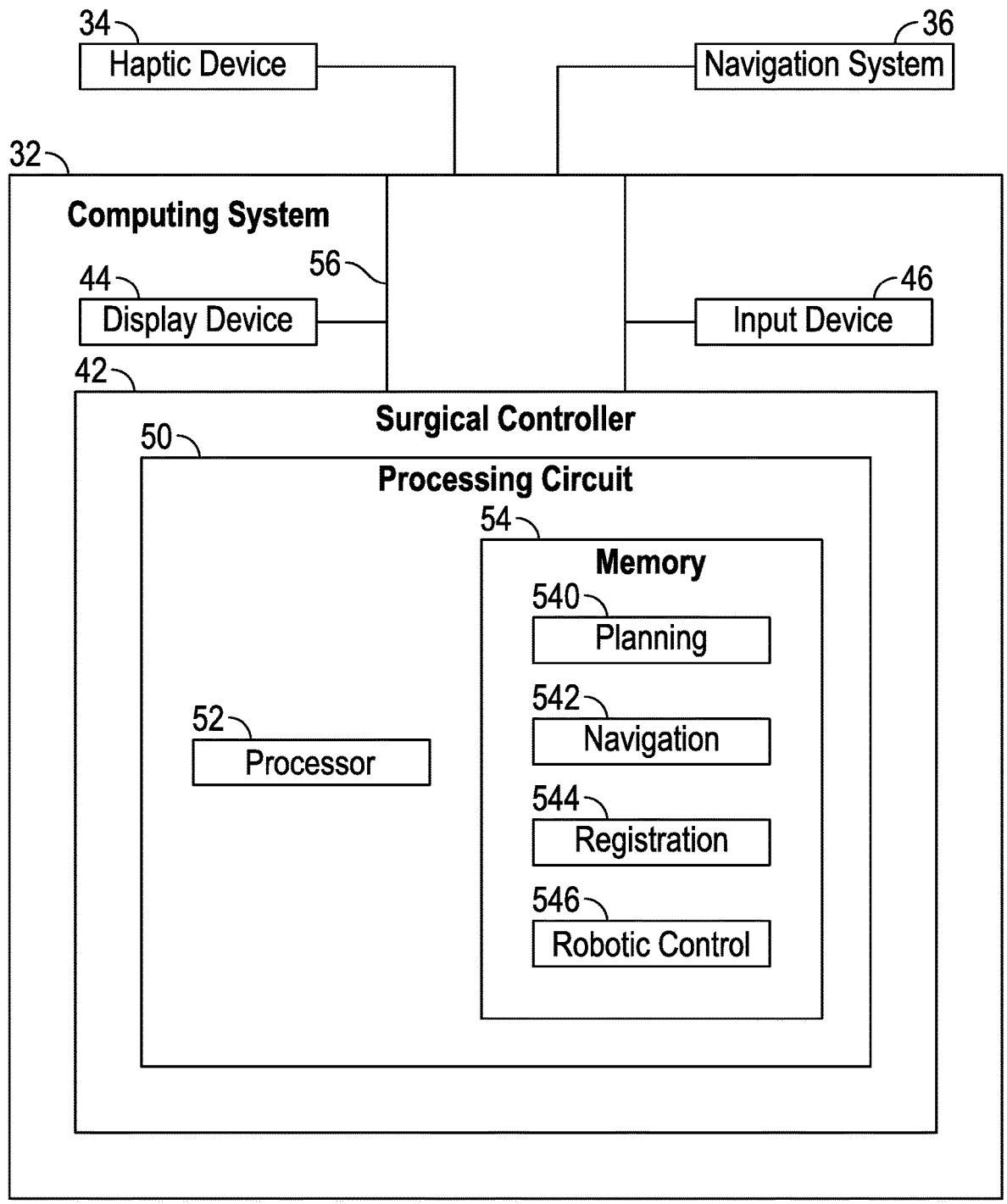
FIG. 7 is a block diagram of a model surgical system according to an exemplary embodiment.

The computing system 32 includes hardware and software for operation and control of the surgical system 30. Such hardware and/or software is configured to enable the system 30 to perform the techniques described herein. The computing system 32 includes a surgical controller 42, a display device 44, and an input device 46. Referring to FIG. 7, in an exemplary embodiment, the surgical controller 42 includes a processing circuit 50 having a processor 52 and memory 54. Processor 52 can be implemented as a general purpose processor, an application specific integrated circuit (ASIC), one or more field programmable gate arrays (FPGAs), a group of processing components, or other suitable electronic processing components. Memory 54 (e.g., memory, memory unit, storage device, etc.) is one or more devices (e.g., RAM, ROM, Flash-memory, hard disk storage, etc.) for storing data and/or computer code for completing or facilitating the various processes described in the present application. Memory 54 may be or include volatile memory or non-volatile memory. Memory 54 may include database components, object code components, script components, or any other type of information structure for supporting the various activities described in the present application. According to an exemplary embodiment, memory 54 is communicably connected to processor 52 and includes computer code for executing one or more processes described herein. The memory 54 may contain a variety of modules, each capable of storing data and/or computer code related to specific types of functions. In one embodiment, memory 54 contains several modules related to surgical procedures, such as a planning module 540, a navigation module 542, a registration module 544, and a robotic control module 546. One such module may contain a configuration database in which spinal plate information is stored including dimensions of various spinal plates, to be used for surgical planning of the sculpted area of bone.

Referring still to FIG. 7, the surgical controller 42 further includes a communication interface 56. The communication interface 56 can be or include wired or wireless interfaces (e.g., jacks, antennas, transmitters, receivers, transceivers, wire terminals, etc.) for conducting data communications with external sources via a direct connection or a network connection (e.g., an Internet connection, a LAN, WAN, or WLAN connection, etc.).

The surgical controller 42 may be any known computing system but is preferably a programmable, processor-based system. For example, the surgical controller 42 may include a microprocessor, a hard drive, random access memory (RAM), read only memory (ROM), input/output (I/O) circuitry, and any other known computer component. The surgical controller 42 is preferably adapted for use with various types of storage devices (persistent and removable), such as, for example, a portable drive, magnetic storage, solid state storage (e.g., a flash memory card), optical storage, and/or network/Internet storage. The surgical controller 42 may comprise one or more computers, including, for example, a personal computer or a workstation operating under a suitable operating system and preferably includes a graphical user interface (GUI).

The display device 44 is a visual interface between the computing system 32 and the user. The display device 44 is connected to the surgical controller 42 and may be any device suitable for displaying text, images, graphics, and/or other visual output. For example, the display device 44 may include a standard display screen (e.g., LCD, CRT, plasma, etc.), a touch screen, a wearable display (e.g., eyewear such as glasses or goggles), a projection display, a head-mounted display, a holographic display, and/or any other visual output device. The display device 44 may be disposed on or near the surgical controller 42 (e.g., on the cart as shown in FIG. 6) or may be remote from the surgical controller 42 (e.g., mounted on a stand with the navigation system 36). The display device 44 is preferably adjustable so that the user can position/reposition the display device 44 as needed during a surgical procedure. For example, the display device 44 may be disposed on an adjustable arm (not shown) or to any other location well-suited for ease of viewing by the user. As shown in FIG. 6 there may be more than one display device 44 in the surgical system 30.

The display device 44 may be used to display any information useful for a medical procedure, such as, for example, images of anatomy generated from an image data set obtained using conventional imaging techniques, graphical models (e.g., CAD models of spinal plates, such as spinal plate 10, implants, instruments, anatomy, etc.), graphical representations of a tracked object (e.g., anatomy, tools, spinal plates, such as spinal plate 10, implants, etc.), constraint data (e.g., axes, articular surfaces, etc.), representations of implant components, spinal plates, such as spinal plate 10, digital or video images, registration information, calibration information, patient data, user data, measurement data, software menus, selection buttons, status information, and the like.

In addition to the display device 44, the computing system 32 may include an acoustic device (not shown) for providing audible feedback to the user. The acoustic device is connected to the surgical controller 42 and may be any known device for producing sound. For example, the acoustic device may comprise speakers and a sound card, a motherboard with integrated audio support, and/or an external sound controller. In operation, the acoustic device may be adapted to convey information to the user. For example, the surgical controller 42 may be programmed to signal the acoustic device to produce a sound, such as a voice synthesized verbal indication "DONE," to indicate that a step of a surgical procedure is complete. Similarly, the acoustic device may be used to alert the user to a sensitive condition, such as producing a tone to indicate that a surgical cutting tool is nearing a critical portion of soft tissue.

The input device 46 of the computing system 32 enables the user to communicate with the surgical system 30. The input device 46 is connected to the surgical controller 42 and may include any device enabling a user to provide input to a computer. For example, the input device 46 can be a known input device, such as a keyboard, a mouse, a trackball, a touch screen, a touch pad, voice recognition hardware, dials, switches, buttons, a trackable probe, a foot pedal, a remote control device, a scanner, a camera, a microphone, and/or a joystick. For example, the input device 46 allows a user to move one or more components displayed on display device 44 based on one or more constraints, as described above, for planning the implant installation.

The communication interface 56 of the computing system 32 is coupled to a computing device (not shown) of the haptic device 34 via an interface and to the navigation system 36 via an interface. The interfaces can include a physical interface and a software interface. The physical interface may be any known interface such as, for example, a wired interface (e.g., serial, USB, Ethernet, CAN bus, and/or other cable communication interface) and/or a wireless interface (e.g., wireless Ethernet, wireless serial, infrared, and/or other wireless communication system). The software interface may be resident on the surgical controller 42, the computing device (not shown) of the haptic device 34, and/or the navigation system 36. In some embodiments, the surgical controller 42 and the computing device (not shown) are the same computing device. The software may also operate on a remote server, housed in the same building as the surgical system 30, or at an external server site.

The system 30 also includes a tracking (or localizing) system 36 that is configured to determine a pose (i.e., position and orientation) of one or more objects during a surgical procedure to detect movement of the object(s). For example, the tracking system 36 may include a detection device that obtains a pose of an object with respect to a coordinate frame of reference of the detection device. As the object moves in the coordinate frame of reference, the detection device tracks the pose of the object to detect (or enable the surgical system 30 to determine) movement of the object. As a result, the computing system 32 can capture data in response to movement of the tracked object or objects. Tracked objects may include, for example, tools/instruments, patient anatomy, such as the targeted vertebrae and the cage 20 as tracked by tracking array 22, implants/prosthetic devices, and components of the surgical system 30. Using pose data from the tracking system 36, the surgical system 30 is also able to register (or map or associate) coordinates in one space to those in another to achieve spatial alignment or correspondence (e.g., using a coordinate transformation process as is well known). Objects in physical space may be registered to any suitable coordinate system, such as a coordinate system being used by a process running on the surgical controller 42 and/or the computer device of the haptic device 34. For example, utilizing pose data from the tracking system 36, the surgical system 30 is able to associate the physical anatomy, such as the patient's spine, with a representation of the anatomy (such as an image displayed on the display device 44). Based on tracked object and registration data, the surgical system 30 may determine, for example, a spatial relationship between the image of the anatomy and the relevant anatomy. In the present method, because resection to form cavity 24 is being performed on two adjacent vertebrae that can move independently, both of the vertebrae must be registered and tracked via the tracking system 36. This is accomplished by registering portions of the vertebrae relative to the tracking array 22. Thus, the relationship between the tracking array 22 and the vertebrae is known, and the detection device is able to track the pose of the tracking array 22 to also track the associated vertebrae. In this way, by also tracking other aspects of the surgical system, such as the surgical tool, the relationship between the tool and each of the target vertebrae can be determined during the surgical procedure.

Registration may include any known registration technique, such as, for example, image-to-image registration (e.g., monomodal registration where images of the same type or modality, such as fluoroscopic images or MR images, are registered and/or multimodal registration where images of different types or modalities, such as MIII and CT, are registered); image-to-physical space registration (e.g., image-to-patient registration where a digital data set of a patient's anatomy obtained by conventional imaging techniques is registered with the patient's actual anatomy); and/or combined image-to-image and image-to-physical-space registration (e.g., registration of preoperative CT and MRI images to an intraoperative scene). Due to the profound landmarks present on the spine, registration of the spinal anatomy may be relatively straightforward. The landmarks of the spine provide clear and accessible points to use for registration of, for example, an image of the patient's anatomy to the patient's anatomy in the physical space. The computing system 32 may also include a coordinate transform process for mapping (or transforming) coordinates in one space to those in another to achieve spatial alignment or correspondence. For example, the surgical system 30 may use the coordinate transform process to map positions of tracked objects (e.g., patient anatomy, etc.) into a coordinate system used by a process running on the computer of the haptic device and/or the surgical controller 42. The coordinate transform process may include any suitable transformation technique, such as, for example, rigid-body transformation, non-rigid transformation, affine transformation, and the like.

The tracking system 36 may be any tracking system that enables the surgical system 30 to continually determine (or track) a pose of the relevant anatomy of the patient. For example, the tracking system 36 may include a non-mechanical tracking system, a mechanical tracking system, or any combination of non-mechanical and mechanical tracking systems suitable for use in a surgical environment. The non-mechanical tracking system may include an optical (or visual), magnetic, radio, or acoustic tracking system. Such systems typically include a detection device adapted to locate in predefined coordinate space specially recognizable trackable elements (or trackers) that are detectable by the detection device and that are either configured to be attached to the object to be tracked or are an inherent part of the object to be tracked. In the embodiments shown in the figures, the trackable element (such as tracking array 22) may include an array of markers having a unique geometric arrangement and a known geometric relationship to the tracked object (the cage 20, and thus the adjacent vertebrae) when the trackable element is attached to the tracked object. The known geometric relationship may be, for example, a predefined geometric relationship between the trackable element and an endpoint and axis of the tracked object. Thus, the detection device can recognize a particular tracked object, at least in part, from the geometry of the markers (if unique), an orientation of the axis, and a location of the endpoint within a frame of reference deduced from positions of the markers.

The markers may include any known marker, such as, for example, extrinsic markers (or fiducials) and/or intrinsic features of the tracked object. Extrinsic markers are artificial objects that are attached to the patient (e.g., markers affixed to skin, markers implanted in bone, stereotactic frames, etc.) and are designed to be visible to and accurately detectable by the detection device. Intrinsic features are salient and accurately locatable portions of the tracked object that are sufficiently defined and identifiable to function as recognizable markers (e.g., landmarks, outlines of anatomical structure, shapes, colors, or any other sufficiently recognizable visual indicator). The markers may be located using any suitable detection method, such as, for example, optical, electromagnetic, radio, or acoustic methods as are well known. For example, an optical tracking system having a stationary stereo camera pair sensitive to infrared radiation may be used to track markers that emit infrared radiation either actively (such as a light emitting diode or LED) or passively (such as a spherical marker with a surface that reflects infrared radiation). Similarly, a magnetic tracking system may include a stationary field generator that emits a spatially varying magnetic field sensed by small coils integrated into the tracked object.

Figure 8:
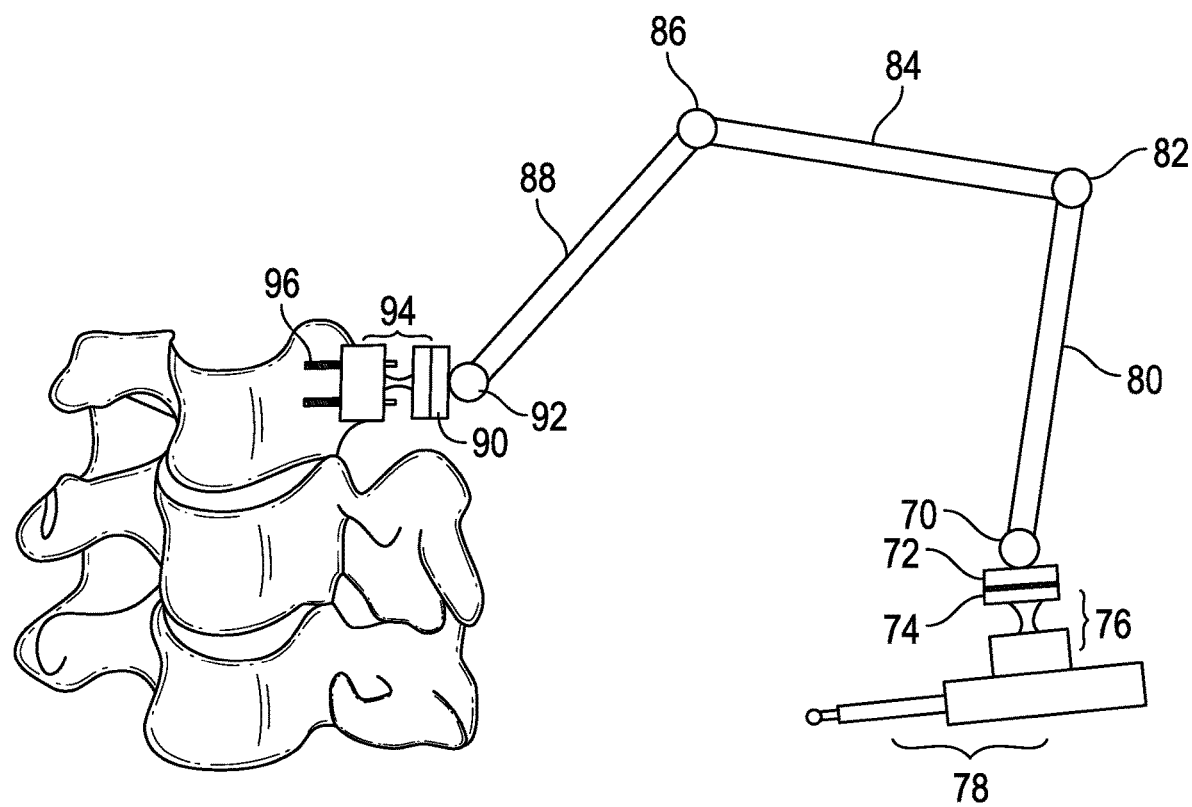
FIG. 8 illustrates a mechanical tracker to track the position of the surgical cutting tool relative to the anatomy according to an exemplary embodiment.

Due to the size constraint and the sensitivity of the spinal anatomy, and other considerations, some of the more robust tracking mechanisms and markers may not be feasible for application in vertebral resection. In another embodiment, a mechanical tracking system, such as that disclosed in U.S. patent application Ser. No. 13/276,048 entitled "System and Method for Surgical Tool Tracking" filed Oct. 18, 2011, which is hereby incorporated by reference in its entirety, may be used. One such embodiment is shown in FIG. 8, where a surgical instrument is operatively coupled to a portion of the spine by a mechanical tracker configuration that is local to the operating theater (i.e., it is directly coupled between the surgical instrument 78 and the anatomy directly around the subject of intervention, here the spinal column). In the depicted embodiment, the surgical instrument 78 is coupled to the mechanical tracker by an instrument fastener comprising a kinematic interface member 74 that is removably attached to a similar kinematic interface member 72 comprising the distal end of the mechanical tracker. This distal kinematic interface member 72 preferably is coupled, via a rotatable joint 70, to an elongate member 80 that has proximal and distal ends. The proximal end in the depicted embodiment is coupled via another joint 82 to another elongate member 84 having proximal and distal ends, the proximal end of which is coupled, via another joint 86, to a third elongate member 88 which has proximal and distal ends. The proximal end of the most proximal elongate member 88 is coupled to a kinematic interface member 90 by another rotatable joint 92. A skeletal fastener 94 is coupled between the vertebrae and the proximal end of the mechanical tracker. One or more pins 96 are utilized to fasten the skeletal fastener 94 to the tissue of the vertebrae, while a kinematic interface member 98 is interfaced with the similar kinematic interface member 90 of the proximal end of the mechanical tracker linkage. With adequate degrees of freedom and ranges of motion at each rotatable joint 70, 82, 86, 92 and an understanding of the rotational activity at each such joint, it is possible to have a real-time or near-real-time understanding of the three dimensional spatial positioning and rotation of the instrument relative to the subject anatomy. An understanding of the rotational activity at each joint may be achieved through the use of joint rotation sensors. In a preferred embodiment, the joint rotation sensors are encoders, such as precision digital encoders. Each encoder preferably comprises or is operatively coupled to an encoder board, which may be coupled to a processing circuit and memory device configured to assist with operation of the encoder and enable it to be operatively coupled, for example, via a wire lead or wireless communication link, to a computing system, such as computing system 32.

This understanding of the rotational activity of the joints may be utilized, for example, to follow a specific surgical plan, such as, to create the cavity 24, having cavity portions 24a, 24b, on the two adjacent vertebrae in accordance with a preoperative or intraoperative plan to achieve the desired relationship between the two vertebrae. While the depicted embodiment shows three elongate members 80, 84, 88 that are rotatably coupled to each other and to fastening configurations 76, 94 other embodiments may contain more or less elongate members and/or joints. Preferably the elongate members are light in weight for relatively low inertial overhead during movement of the surgical tool 78, and are substantially rigid, so that certain assumptions about their deflection during use of the mechanical linkage may be utilized (in another embodiment, they may be more flexible if the flexibility can be characterized with strain gauges or the like, so that deflection of the linkage may be incorporated into the determination of positions and orientations of portions of the linkage).

Referring back to FIG. 6, such a mechanical linkage configuration may be utilized in corporation with the surgical system 30. The depicted instrument 78 may be coupled to the mechanical linkage (and thereby the spine) of the configuration of FIG. 8, while such instrument 78 also remains coupled to a base controller subsystem which comprises a computerized controller such as a processor or microcontroller, and carrying haptic device 34. Surgical system 30 and haptic device 34 may also be configured for use with the optical tracking system described above, utilizing at least tracking array 22 attached to cage 20.

The robotic arm of haptic device 34 may comprise one or more servo motors controlled by the computerized controller, and these servo motors may be selectively activated by the controller to enforce motion limitations upon the surgical instrument 78, such as by providing haptic feedback to an operator whose hand is trying to move the surgical instrument 78 held by haptic device 34 (and in some embodiments, the mechanical linkage of FIG. 8), or by providing corrective motion as an operator tries to move the surgical instrument 78 along a path that strays from a predetermined boundary planned according to the desired placement of the spinal plate 10 relative to the pertinent tissue structures. Where mechanical linkage is used, preferably the kinematics of the instrument support structure and the mechanical tracker linkage may be configured to not spatially intersect or collide with each other for the useful ranges of motion of the surgical instrument 78 in the operating workspace. Such a mechanical linkage configuration also may be utilized in corporation with a freehand surgical tool (i.e., not supported by an instrument support structure).

The haptic device 34 may be the Tactile Guidance System™ (TGS™) manufactured by MAKO Surgical Corp., and used to prepare the surface of the patient's bone for insertion of the spinal plate 10. The haptic device 34 provides haptic (or tactile) guidance to guide the surgeon during a surgical procedure. The haptic device is an interactive surgical robotic arm that holds a surgical tool (e.g., a surgical burr) and is manipulated by the surgeon to perform a procedure on the patient, such as cutting a surface of a bone in preparation for spinal plate installation. As the surgeon manipulates the robotic arm to move the tool and sculpt the bone, the haptic device 34 guides the surgeon by providing force feedback that constrains the tool from penetrating a virtual boundary.

For example, the surgical tool is coupled to the robotic arm and registered to the patient's anatomy. The surgeon operates the tool by manipulating the robotic arm to move the tool and perform the cutting operation. As the surgeon cuts, the navigation system 36, tracks the location of the tool and the patient's anatomy. In most cases, the haptic device 34 allows the surgeon to freely move the tool in the workspace. However, when the tool is in proximity to the virtual boundary (which is also registered to the patient's anatomy), the haptic device 34 controls the haptic device to provide haptic guidance (e.g., force feedback) that tends to constrain the surgeon from penetrating the virtual boundary with the tool.

The virtual boundary may represent, for example, a cutting boundary defining a region of bone to be removed, such as cavity 24 for receiving a spinal plate 10, or a virtual pathway for guiding the surgical tool to a surgical site without contacting critical anatomical structures, which may be especially useful for the challenging approach given the anatomical structure of the lumbar spine region. The virtual boundary may be defined by a haptic object and the haptic guidance may be in the form of force feedback (i.e., force and/or torque) that is mapped to the haptic object and experienced by the surgeon as resistance to further tool movement in the direction of the virtual boundary. Thus, the surgeon may feel the sensation that the tool has encountered a physical object, such as a wall. In this manner, the virtual boundary functions as a highly accurate virtual cutting guide. For example, the virtual boundary can represent a region of bone to be removed for properly fitting the spinal plate 10 to the patient's target vertebrae as planned through the planning procedure described below. Such virtual boundaries can help to ensure the efficient and accurate removal of portions of a patient's anatomy, which may include preparing bone and/or disc space, to accurately fit implant components based on a customized plan for the patient. This also ensures that the actual placement of the spinal plate 10 meets the constraints that were used in planning.

The surgical system 30 includes a visual display (e.g., the display device 44) which can show the amount of bone removed during the cutting operation. Because the haptic device 34 utilizes tactile force feedback, the haptic device 34 can supplement or replace direct visualization of the surgical site and enhance the surgeon's natural tactile sense and physical dexterity. Guidance from the haptic device 34 coupled with computer aided surgery (CAS), enables the surgeon to actively and accurately control surgical actions (e.g., bone cutting) to achieve the tolerances and complex bone resection shapes that enable optimal and customized installation of implants, such as spinal plate 10.

In a preferred embodiment, surgical planning is accomplished using the surgical system 30. For example, as described above, the surgeon may use the surgical planning features of the computing system 32 to plan the placement of the spinal plate 10 by placing a representation of the plate to a preoperative CT image (or other image or model of the anatomy), to define the virtual boundary of the region of bone to be removed, or to define an area to create pre-drilled holes in the bone for receiving engagement member 18. Planning the placement of the spinal plate 10 may be based on a desired relationship between two adjacent vertebrae. The plan involves planning resections on both of the vertebrae, independent of the other. The software enables the surgeon to view the placement of the plate 10 relative to the anatomy. The representation of the plate used during surgical planning may represent spinal plate 10, as described above, or represent any spinal plate having its design in the computing system 32 database containing a variety of spinal plates that may be implanted on the patient's spine. Based on the planned placement of the spinal plate, the haptic device 34 software generates one or more haptic objects, which create one or more virtual boundaries representing, for example, a portion of bone to be removed to sculpt cavity 24, including cavity portion 24a on a first vertebrae and cavity portion 24b on a second, adjacent vertebrae, the location of pre-drilled holes, or critical anatomy to be avoided based at least in part on the placement of the spinal plate. The haptic objects may also create a virtual boundary representing an area of the vertebral disc space to be removed to perform a cervical or lumbar discectomy. During surgery, the haptic object is registered to the anatomy of the patient, such as to the spine. By providing force feedback, the haptic device 34 enables the surgeon to interact with the haptic object in the virtual environment. In this manner, the haptic device 34 haptically guides the surgeon during bone preparation to sculpt or contour the appropriate location of the bone so that a shape of the bone substantially conforms to a shape of the spinal plate. The haptic device 34 may further haptically guide the surgeon to prepare pre-drilled holes in the bone to conform with the areas of the spinal plate wherein engagement members may be received.

Figure 9:
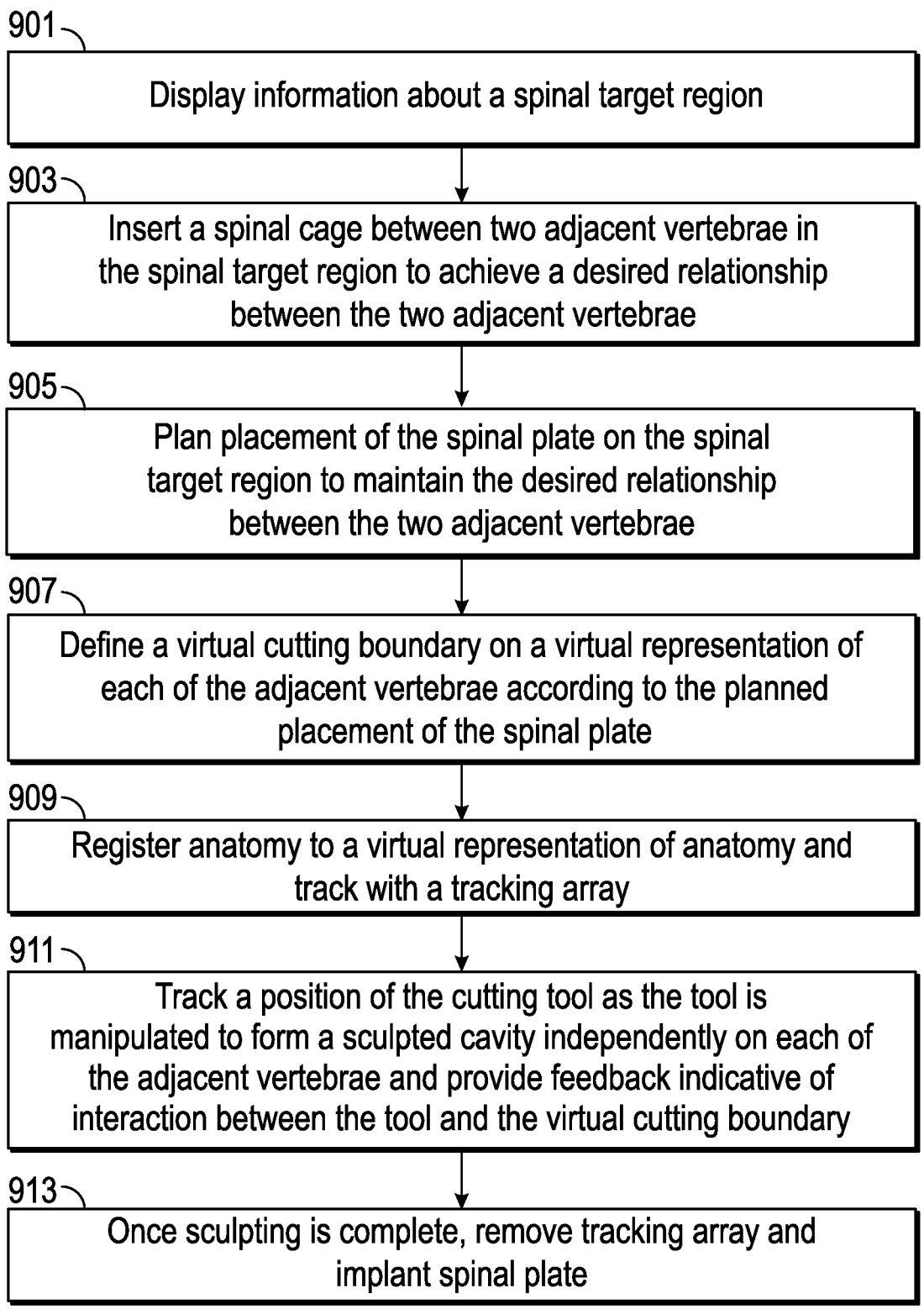
FIG. 9 illustrates steps of a spinal plate implantation procedure according to an exemplary embodiment.

FIG. 9 describes an embodiment of a method of implanting a spinal plate on a patient's spine. In step 901, information about a spinal target region is displayed, for example, the relevant images of the patient's anatomy acquired by a preoperative CT scan or a bone model and saved in the computer system 32 may be loaded and displayed on display screen 44. Similarly, a representation of a spinal plate, such as spinal plate 10 may be obtained. Information and images of the spinal plate 10 to be implanted may also be displayed. Then, as described above, the spinal cage 20 is inserted between two adjacent vertebrae to achieve a desired relationship and obtain a desired alignment of the spinal area (step 903). In step 905, also as described above, surgical planning may be performed to determine and plan proper placement of the spinal plate on the spinal target region to maintain the desired relationship between two adjacent vertebrae, as well as create a plan for bone preparation. Step 907 includes defining a virtual cutting boundary for a cutting tool relative to the virtual representations of the adjacent vertebrae according to the planned placement of the spinal plate 10. In step 909, a registration method is used to associate the physical anatomy, such as the patient's spine, with the representation of the anatomy, which may be achieved by using a tracking array 22 coupled to the spinal cage 20 positioned between the vertebrae. The surgeon can then prepare the bone for implantation of the spinal plate 10 according to the surgical plan by manipulating the tool, such as a surgical burr, to sculpt cavity 24, including sculpting cavity portions 24a, 24b independently in each of the adjacent vertebrae and, optionally prepare pre-drilled holes 26 in the bone (step 911). During bone preparation (step 911), the system may track a position of the surgical tool relative to the anatomy and/or the virtual cutting boundary and provide feedback, such as haptic feedback, indicative of interaction between the cutting tool and the virtual cutting boundary to limit manipulation of the tool outside of the virtual cutting boundary. Once the bone has been prepared, the surgeon can remove the racking array 22, install the spinal plate 10, and secure the spinal plate 10 within cavity 24, preferably by at least one engagement member 18 (step 913). The method of FIG. 9 may allow implantation of a spinal plate 10 having a very low profile above the bone surface.

In other fusion applications such as ankle, hand/wrist, and other joint fusion procedures, and craniofacial fusion procedures, a similar method can be employed to obtain information about the target bones, to plan placement of a fusion plate to achieve a desired relationship, and prepare the target bones to receive a fusion plate to thereby help with maintaining the desired relationship between the bones of the joint or target area. Though the present disclosure is directed to the above-described spinal fusion procedure, it is contemplated that the systems and methods described above could also be applied to various other procedures, such as those listed.

The above-described systems and methods can be implemented in digital electronic circuitry, in computer hardware, firmware, and/or software. The implementation can be as a computer program product (i.e., a computer program tangibly embodied in an information carrier). The implementation can, for example, be in a machine-readable storage device, for execution by, or to control the operation of, a data processing apparatus. The implementation can, for example, be a programmable processor, a computer, and/or multiple computers.

A computer program can be written in any form of programming language, including compiled and/or interpreted languages, and the computer program can be deployed in any form, including as a stand-alone program or as a subroutine, element, and/or other unit suitable for use in a computing environment. A computer program can be deployed to be executed on one computer or on multiple computers at one site.

Method steps can be performed by one or more programmable processors executing a computer program to perform functions of the invention by operating on input data and generating output. Method steps can also be performed by and an apparatus can be implemented as special purpose logic circuitry. The circuitry can, for example, be a FPGA (field programmable gate array) and/or an ASIC (application-specific integrated circuit). Modules, subroutines, and software agents can refer to portions of the computer program, the processor, the special circuitry, software, and/or hardware that implements that functionality.

Processors suitable for the execution of a computer program include, by way of example, both general and special purpose microprocessors, and any one or more processors of any kind of digital computer. Generally, a processor receives instructions and data from a read-only memory or a random access memory or both. The essential elements of a computer are a processor for executing instructions and one or more memory devices for storing instructions and data. Generally, a computer can include, can be operatively coupled to receive data from and/or transfer data to one or more mass storage devices for storing data (e.g., magnetic, magnetooptical disks, or optical disks).

Data transmission and instructions can also occur over a communications network. Information carriers suitable for embodying computer program instructions and data include all forms of non-volatile memory, including by way of example semiconductor memory devices. The information carriers can, for example, be EPROM, EEPROM, flash memory devices, magnetic disks, internal hard disks, removable disks, magneto-optical disks, CD-ROM, and/or DVD-ROM disks. The processor and the memory can be supplemented by, and/or incorporated in special purpose logic circuitry.

To provide for interaction with a user, the above described techniques can be implemented on a computer having a display device. The display device can, for example, be a cathode ray tube (CRT) and/or a liquid crystal display (LCD) monitor. The interaction with a user can, for example, be a display of information to the user and a keyboard and a pointing device (e.g., a mouse or a trackball) by which the user can provide input to the computer (e.g., interact with a user interface element). Other kinds of devices can be used to provide for interaction with a user. Other devices can, for example, be feedback provided to the user in any form of sensory feedback (e.g., visual feedback, auditory feedback, or tactile feedback). Input from the user can, for example, be received in any form, including acoustic, speech, and/or tactile input.

The above described techniques can be implemented in a distributed computing system that includes a back-end component. The back-end component can, for example, be a data server, a middleware component, and/or an application server. The above described techniques can be implemented in a distributing computing system that includes a front-end component. The front-end component can, for example, be a client computer having a graphical user interface, a Web browser through which a user can interact with an example implementation, and/or other graphical user interfaces for a transmitting device. The components of the system can be interconnected by any form or medium of digital data communication (e.g., a communication network). Examples of communication networks include a local area network (LAN), a wide area network (WAN), the Internet, wired networks, and/or wireless networks.

The system can include clients and servers. A client and a server are generally remote from each other and typically interact through a communication network. The relationship of client and server arises by virtue of computer programs running on the respective computers and having a client-server relationship to each other.

The transmitting device can include, for example, a computer, a computer with a browser device, a telephone, an IP phone, a mobile device (e.g., cellular phone, personal digital assistant (PDA) device, laptop computer, electronic mail device), and/or other communication devices. The browser device includes, for example, a computer (e.g., desktop computer, laptop computer) with a browser.

One skilled in the art will realize the invention may be embodied in other specific forms without departing from the spirit or essential characteristics thereof. The foregoing embodiments are therefore to be considered in all respects illustrative rather than limiting of the invention described herein. Scope of the invention is thus indicated by the appended claims, rather than by the foregoing description, and all changes that come within the meaning and range of equivalency of the claims are therefore intended to be embraced therein.

What is claimed is:

1. A method, comprising:
    tracking one or more of a plurality of vertebrae of a patient;
    adjusting a relationship between the plurality of vertebrae to a desired rotation between the plurality of vertebrae;
    creating an implant placement plan based on the adjusted relationship, the implant placement plan comprising a placement of a spinal plate across the plurality of vertebrae; and
    robotically preparing the plurality of vertebrae to receive the spinal plate in accordance with the implant placement plan.

2. The method of claim 1, wherein the plurality of vertebrae comprise three or more vertebrae.

3. The method of claim 1, wherein:
tracking the one or more of the plurality of vertebrae of the patient comprises collecting data indicative of positions of the plurality of vertebrae; and
creating the implant placement plan comprises determining the adjusted relationship based on the data.

4. The method of claim 3, wherein collecting the alignment data is performed while one or more spacers are positioned at the plurality of vertebrae.

5. The method of claim 1, wherein robotically preparing the plurality of vertebrae to receive the implant comprises:
tracking a pose of a robotic device relative to the plurality of vertebrae; and
controlling the robotic device based on the pose of the robotic device relative to the plurality of vertebrae.

6. The method of claim 5, wherein controlling the robotic device comprises providing force feedback via the robotic device.

7. The method of claim 5, wherein creating the implant placement plan comprises defining a virtual cutting boundary; and
controlling the robotic device comprises confining the pose of the robotic device based on the virtual cutting boundary.

8. The method of claim 7, wherein the virtual cutting boundary corresponds to a shape of the spinal plate.

9. The method of claim 1, wherein robotically preparing the plurality of vertebrae to receive the spinal plate comprises forming a sculpted cavity at a first vertebrae of the plurality of vertebrae, the sculpted cavity corresponding to a surface of the spinal plate.

10. The method of claim 1, wherein robotically preparing the plurality of vertebrae comprises creating a hole in a first vertebrae of the plurality of vertebrae, the hole configured to receive an engagement member of the spinal plate.

11. The method of claim 1, wherein adjusting the relationship between the plurality of vertebrae includes adjusting the plurality of vertebrae to a desired distance between the plurality of vertebrae.

12. The method of claim 1, wherein adjusting the relationship between the plurality of vertebrae includes adjusting the plurality of vertebrae to a desired alignment between the plurality of vertebrae.

13. A robotically-assisted surgical system, comprising:
a tracking system configured to track one or more of a plurality of vertebrae of a patient; and
a robotic device configured to modify the plurality of vertebrae;
a processing circuit configured to:
obtain an adjusted relationship to a desired rotation between the plurality of vertebrae;
obtain an implant placement plan based on the adjusted relationship, wherein the implant placement plan comprises a placement of a spinal plate across the plurality of vertebrae; and
control the robotic device to prepare the plurality of vertebrae to receive the spinal plate in accordance with the implant placement plan.

14. The robotically-assisted surgical system of claim 13, wherein the plurality of vertebrae comprise three or more vertebrae.

15. The robotically-assisted surgical system of claim 13, wherein the tracking system is configured to provide data indicative of a current alignment of the plurality of vertebrae; and
wherein the processing circuit is configured to obtain the adjusted relationship of the plurality of vertebrae using the data.

16. The robotically-assisted surgical system of claim 15, comprising a spacer configured to be inserted between adjacent vertebrae of the plurality of vertebrae; and
wherein the tracking system is configured to collect the data while the spacer is between the adjacent vertebrae of the plurality of vertebrae.

17. The robotically-assisted surgical system of claim 13, wherein the tracking system is configured to track a pose of the robotic device relative to the plurality of vertebrae; and
the processing circuit is configured to control the robotic device based on the pose for the robotic device relative to the plurality of vertebrae.

18. The robotically-assisted surgical system of claim 13, wherein the processing circuit is configured to control the robotic device to provide force feedback to a user of the robotic device.

19. The robotically-assisted surgical system of claim 13, wherein the implant placement plan comprises a virtual cutting boundary; and
the processing circuit is configured to control the robotic device based on the virtual cutting boundary.

20. The robotically-assisted surgical system of claim 19, wherein the virtual cutting boundary corresponds to a shape of the spinal plate.

21. The robotically-assisted surgical system of claim 13, wherein the robotic device is configured to prepare the plurality of vertebrae by forming a sculpted cavity at a first vertebrae of the plurality of vertebrae, the sculpted cavity corresponding to a surface of the spinal plate.

22. The robotically-assisted surgical system of claim 21, wherein the robotic device is configured to prepare the plurality of vertebrae by creating a hole in a first vertebrae of the plurality of vertebrae, the hole configured to receive an engagement member of the spinal plate.

* * * * *